United States Patent [19]
Gadonniex et al.

[11] Patent Number: 5,538,003
[45] Date of Patent: Jul. 23, 1996

[54] QUICK METHOD AND APPARATUS FOR IDENTIFYING A REGION OF INTEREST IN AN ULTRASOUND DISPLAY

[75] Inventors: Sharon Gadonniex, Somerville; Christina E. Banta, Andover; David M. Prater, Melrose, all of Mass.

[73] Assignee: Hewlett-Packard Company, Palo Alto, Calif.

[21] Appl. No.: 443,979

[22] Filed: May 18, 1995

[51] Int. Cl.⁶ ........................................... A61B 8/00
[52] U.S. Cl. ..................... 128/660.09; 128/916
[58] Field of Search .................. 128/661.01, 660.04, 128/660.07, 661.10, 916, 660.09; 73/606, 607, 618, 619, 620; 364/413.25

[56] References Cited

U.S. PATENT DOCUMENTS

| | | | |
|---|---|---|---|
| 4,206,654 | 6/1980 | Keller et al. | 73/620 |
| 4,241,608 | 12/1980 | Dees et al. | 73/606 |
| 5,195,521 | 3/1993 | Melton, Jr. et al. | 128/660.02 |
| 5,257,624 | 11/1993 | Fraser et al. | 128/660.01 |
| 5,285,788 | 2/1994 | Arenson et al. | 128/660.05 |
| 5,322,067 | 6/1994 | Prater et al. | 128/660.07 |

*Primary Examiner*—George Manuel

[57] ABSTRACT

An ultrasound display system enables a user to rapidly identify a region of interest (ROI) in a displayed ultrasound image without having to trace the outline of the ROI. The system includes a display and a processor for causing the display to manifest an ultrasound image. A user entry device enables a user to initiate a "quick ROI" identification procedure which causes the processor to superimpose a closed geometric figure on a displayed ultrasound image. The user entry device further enables adjustment of the closed geometric figure to substantially enclose the ROI. A user selection input device, in response to user actuation, causes the processor to identify the boundary of the ROI that lies within the vicinity of an edge of the closed geometric figure and further enables the processor to carry out calculations with respect to the determined ROI boundary.

10 Claims, 8 Drawing Sheets

5,538,003

QUICK METHOD AND APPARATUS FOR IDENTIFYING A REGION OF INTEREST IN AN ULTRASOUND DISPLAY

FIELD OF THE INVENTION

This invention relates to ultrasound imaging and, more particularly, to a method and apparatus for quickly identifying a region of interest in an ultrasound image.

BACKGROUND OF THE INVENTION

Ultrasound imaging of various aspects of the heart is a well known diagnostic modality. Systems have been designed which enable an ultrasound system to determine the volume of the left ventricle of the heart at various times during the cardiac cycle. Such imaging systems enable identification of a tissue/blood interface and allow a physician to trace the interface and perform calculations regarding blood pumping efficiency and volume. Such systems require an ability to accurately identify the endocardium/blood boundary. In U.S. Pat. No. 5,195,521 to Melton, Jr. et al., assigned to the same assignee as this application, a majority vote circuit indicates, at each range along an ultrasound-scan line, when a majority of the signals for both a current scan line and two previous scan lines indicate that reflections of the transmitted pulses are from tissue or blood. In this manner, the tissue/blood interface is accurately determined and is less affected by noise.

U.S. Pat. No. 5,257,624 to Fraser et al. and assigned to the same assignee as this application, describes a gain control circuit which enables gain along one or more scan lines to be kept substantially constant—thereby enabling a more accurate tissue/blood boundary determination. The accuracy enhancement occurs because the boundary judgement is based upon a discrimination in levels between return pulses, with tissue generally returning a higher level signal than blood. If the gain of return signals from a scan line varies significantly due to tissue attenuation, tissue/blood boundary determination is rendered substantially more complex.

U.S. Pat. No. 5,322,067 to Prater et al. (assigned to the same assignee as this application), describes an improved technique for determining volumetric efficiency of the left ventricle. An ultrasound display of the left ventricle and surrounding tissue is obtained and the user traces a region of interest around the ventricle at the largest volume for which a volume determination is to be made. Each pixel of the ultrasound image within a region of interest is classified as a blood pixel or a tissue pixel. The area of blood pixels within each display frame is determined and the volume of the ventricle is calculated from the area of the fluid pixels within each segment of the region, using the method of disks.

In U.S. patent application Ser. No. 08/308,718 to Koch, III et al., pixel changes from tissue-to-blood or blood-to-tissue are determined over succeeding display frames. For each pixel evidencing a like kind change, a common mapping function is assigned so that all such changed pixels exhibit a common appearance. In the preferred mode, the common appearance is a single color assigned to all changed pixels of a same type (e.g., blood-to-tissue) in a frame. When succeeding frames are compared, there is a binary change in pixel color values between pixels which change type from one frame to the next. Tissue/blood interfaces are thereby clearly visible.

The cardiologist, in assessing heart function, often wishes to know the pumping efficiency of the left ventricle. Existing ultrasound systems require the user to trace the outline of the pumping chamber by generating a boundary around this region of interest with an input device such as a mouse or track ball and to input the traced outline into the system. By knowing the cross section area of the chamber at diastole and systole, the system is than able to determine volumetric changes. Such outline tracing may be time consuming and laborious. Accordingly, there is a need in modern ultrasonography systems for a quick method of constructing a region of interest outline about an ultrasound image and for making flow or volumetric change calculations with respect thereto.

SUMMARY OF THE INVENTION

An ultrasound display system enables a user to rapidly identify a region of interest (ROI) in a displayed ultrasound image without having to trace the outline of the ROI. The system includes a display and a processor for causing the display to manifest an ultrasound image. A user entry device enables a user to initiate a "quick ROI" identification procedure which causes the processor to superimpose a closed geometric figure on a displayed ultrasound image. The user entry device further enables adjustment of the closed geometric figure to substantially enclose the ROI. A user selection input device, in response to user actuation, causes the processor to identify an outline of the ROI that lies within the vicinity of an edge of the closed geometric figure and further enables the processor to carry out calculations with respect to the determined ROI boundary.

DETAILED DESCRIPTION OF THE PREFERRED EMBODIMENT

To provide a display which enables the cardiac wall to be clearly visualized, each pixel is initially classified as to whether it is a tissue pixel or a blood pixel. During succeeding frames of ultrasound imaging, pixel classification changes from tissue-to-blood or blood-to-tissue are indicative of wall segment movement.

Once the image has been differentiated into blood and tissue pixels, the user initiates a "quick ROI" procedure. That procedure, as will be hereinafter understood, enables the user to impose a closed geometric figure (hereafter referred to as a "quick trace") over the displayed ultrasound image, to modify the size and positioning of the quick trace and to position the quick trace so that it includes the ROI of the displayed ultrasound image. The quick ROI procedure automatically selects an image frame appearing at diastole. Thereafter, a processor within the ultrasound instrument searches within the boundary of the quick trace, identifies the actual boundary of the displayed ROI and performs calculations with respect thereto. Further details of the invention will be understood from the following description.

Figure 1:
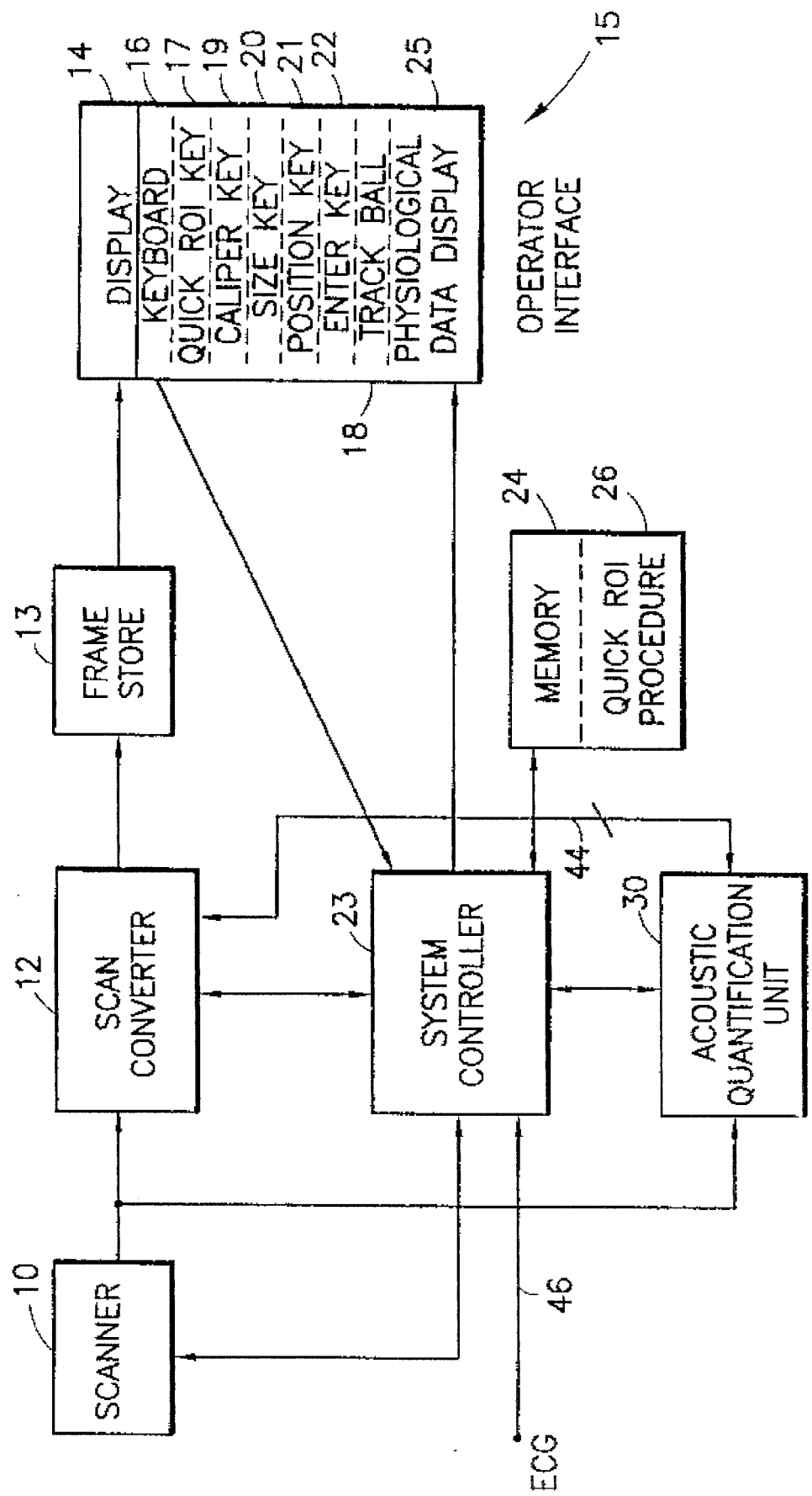
FIG. 1 is a block diagram of an ultrasound imaging system that incorporates the invention.

A block diagram of a system that implements the invention is shown in FIG. 1. A scanner 10 performs ultrasound scanning of a specified region of a patient's body, such as the heart. The scanner includes an ultrasound transducer for transmitting and receiving ultrasound energy. The transducer transmits ultrasound energy into a region being imaged and receives reflected ultrasound energy from organs within the patient's body.

As is well known, the transducer may include an array of transducer elements and by appropriately delaying the pulses applied to each transducer element, a focused ultrasound beam is transmitted along a desired scan line. The reflected ultrasound energy from a given point within the patient's body is received by the transducer elements at different times. The transducer elements converge the received ultrasound energy signals, which signals are supplied to a beam former. The beam former processes the return signals and outputs a signal stream that is indicative of a focused, received, beam. However, the invention may also be employed with a variety of scan-formats, i.e., sector, linear, trapezoidal, etc.

The depth and direction of the focal point of the received beam relative to the ultrasound transducer can be varied dynamically with time by appropriately delaying the received signals from each of the transducer elements. The delayed signals from each transducer element are summed to provide a scanner signal that is a representation of the reflected energy level along a given scan line. The process is repeated for multiple scan lines to provide signals for generating an image of the prescribed region of the patient's body. Typically, the scan pattern is a sector scan (e.g., see FIGS. 4 and 5), wherein the scan lines originate at a point at the center of the ultrasound transducer and fan out at different angles. However, the invention may also be employed with a variety of scan formats, e.g., sector, linear, trapezoidal, etc.

Alternatively, scanner 10 can include a mechanical scanner for ultrasound scanning of a specified region of a patient's body. In such a scanner, an ultrasound transducer is scanned across a specified region by a motor (as is well known in the art).

The output of scanner 10 is applied to a scan converter 12 which converts the sector scan information generated by scanner 10 to a conventional raster scan display. The output of scan converter 12 is stored in a frame store 13 and is then passed to a display 14 which is part of an operator interface 15. Operator interface 15 includes a keyboard 16 and a track ball 18 which is used to control a cursor's position on display 14. Keyboard 16 includes five dedicated keys 17, 19, 20, 21 and 22 denoted "Quick ROI", "Caliper", "Size", "Position" and "Enter" whose functions will be described below. A physiological data display 25 is also provided which includes an alphanumeric display of physiologic data and a display of physiological waveforms, e.g., an ECG trace.

A system controller 23 (i.e., a microprocessor) provides overall control of the ultrasound imaging system. A memory 24 provides data storage for controller 23 and further includes a quick ROI procedure 26 that implements (with controller 23) the invention. An acoustic quantification unit 30 provides a pixel classification capability and enables each pixel in each frame to be classified as to whether it is blood or tissue and further employs an ECG input to determine the pixels which appear at diastole. Acoustic quantification unit 30, in conjunction with controller 23, determines the volume of a fluid filled cavity as described in U.S. Pat. No. 5,322,067 to Prater et al., referred to above. The disclosure of U.S. Pat. No. 5,322,067 is incorporated herein by reference.

Figure 2:
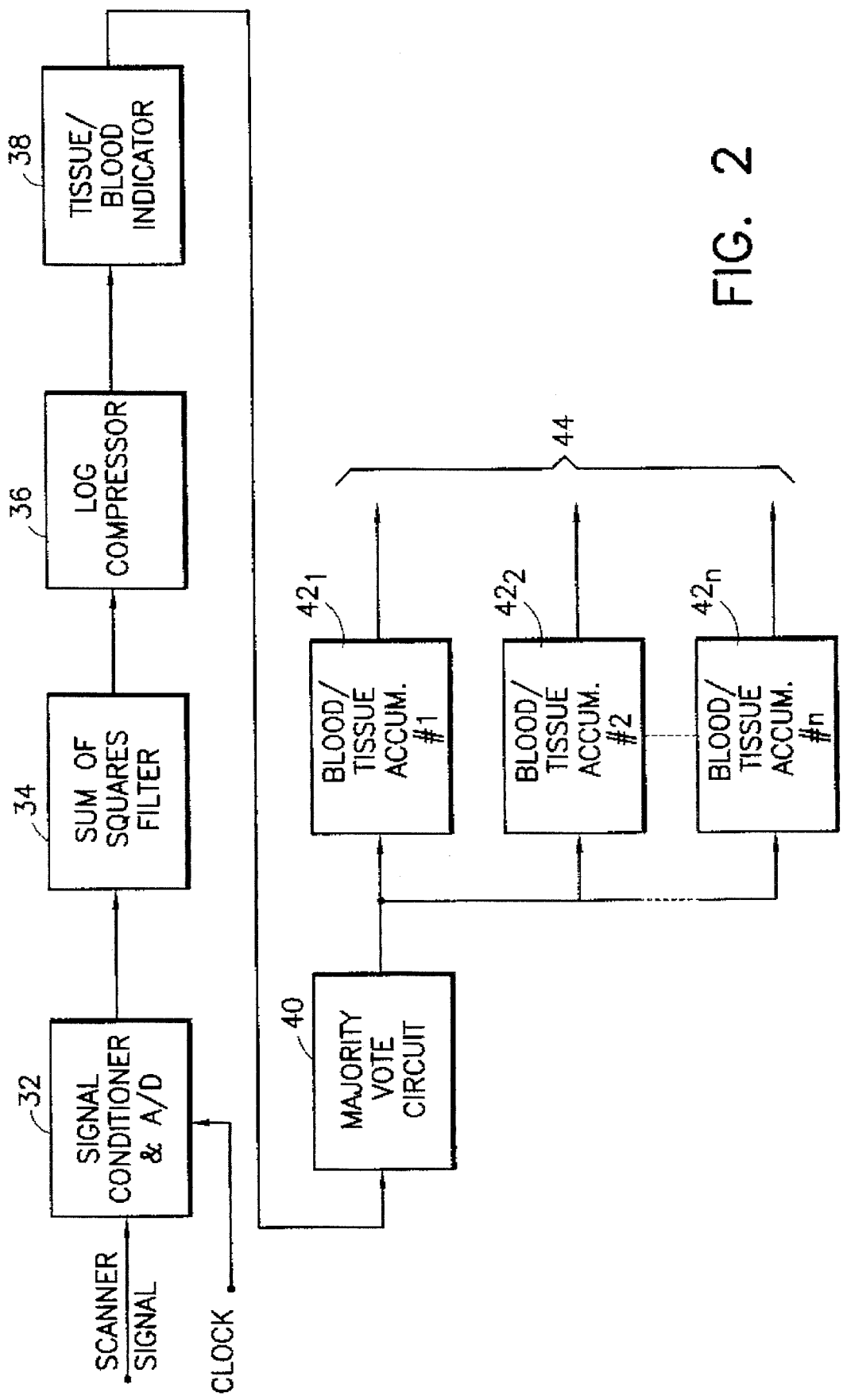
FIG. 2 is a block diagram of an acoustic quantification unit which determines whether a pixel is indicative of a fluid region or a tissue region.

A block diagram of acoustic quantification unit 30 is shown in FIG. 2. A scanner signal from scanner 10 is applied to signal conditioner and analog to digital converter 32 which adjusts the gain of the received scanner signal and converts the analog signal to a series of digital samples. The digital samples are applied to a sum of squares filter 34 which squares the signal and integrates the result, using a moving window. The output of filter 34 is supplied to a log compressor 36 which performs a log compression of the form Y=10 LOG X. As the scanner signal contains noise and reflections which may cause an erroneous tissue/blood decision, the accuracy of the decision is increased by averaging along each scan line. That averaging is performed by sum of squares filter 34.

The output of log compressor 36 is applied to a tissue-blood indicator 38 which compares the digital samples with a reference level. The reference level is selected between an amplitude representative of a blood return and a tissue return amplitude. The output of tissue/blood indicator 38 has a first state when the input signal is representative of blood and a second state when the input signal is representative of tissue. The tissue/blood analysis is applied to each digitized sample input. Thus, for each digitized return sample, a tissue/blood determination is rendered so as to enable a differentiation, frame-to-frame, as to whether a pixel location has changed from blood-to-tissue or vice-versa.

The accuracy of the blood/tissue decision is increased by applying the output of tissue/blood indicator 38 to a majority vote circuit 40. Majority votes circuit 40 performs an effective averaging by comparing decisions for each digitized signal sample with decisions for digitized signal samples at the same depth on adjacent scan lines of the ultrasound image. The result of the majority vote circuit is determined by sate of a majority of the samples considered.

The majority vote process is preferably performed for a group of samples at the same depth on several successive scan lines, typically three, to provide higher accuracy. The number of samples used to perform the majority vote can be varied, depending upon circumstances. Majority vote circuit 40 outputs a signal that is active when the sample is representative of blood and is inactive when the sample is representative of tissue. The use of the majority vote circuit to improve accuracy of a tissue/blood indication is described in detail in U.S. Pat. No. 5,195,521 to Melton, Jr. et al., assigned to the same assignee as this application. The disclosure of U.S. Pat. No. 5,195,521 is incorporated herein by reference.

Each active/inactive output from majority vote circuit 40 is applied to a blood/tissue accumulator $42_1$–$42_n$ where n represents the number of digitized samples along a scan line.

Thus, each blood/tissue accumulator is updated each scan to enable an indication as to whether the digitized sample value represents blood or tissue. The active/inactive outputs from the majority vote circuit 40 are distributed amongst accumulators $42_1$–$42_n$ by a multiplexer arrangement (not shown).

The outputs from, accumulators $42_1$–$42_n$ are applied via lines 44 to scan converter 12 (see FIG. 1). As indicated above, scan converter 12 receives a scan signal from scanner 10, which scanner signal is in the form of "fan-type" or "θ space" presentation. Thus, each scan line is defined by an angle θ. Regions along a scan line are indicative of a depth of penetration of the ultrasound signal.

Within scan converter 12, the θ-space input is converted to an X/Y space pixel representation, which representation is then stored in frame store 13 for subsequent display. Each digitized sample value from accumulators $42_1$–$42_n$ is similarly converted to a blood/tissue value representative of a pixel in X/Y space—using the same conversion process that is employed to convert the θ-space scan values to individual pixel values. Thus, each X/Y pixel stored in frame store 13 includes a further associated value which indicates its blood/tissue state.

An additional classification is performed which indicates, for each frame, at what time during the cardiac cycle, the frame displays. To enable such classification, a digitized ECG input 46 is applied to system controller 23 (FIG. 1). ECG input 46 is analyzed by system controller 23 to enable a determination to be made as to when a value thereof reaches a level indicative of the peak of the R wave. As is known to those skilled in the art, the normal ECG waveform indicates a QRS wave shape, with the R wave being indicative of onset of the systolic cycle. Thus, when system controller 23 determines a maximum value input on line 46, commencement of the systolic cycle is denoted by designating the next display frame from scan converter 12 as frame zero.

Because the peak of the R wave occurs just prior to actual mechanical contraction of the left ventricle, the frame zero image represents the onset of the actual mechanical ventricular contraction. The frame zero input to scan converter 12 enables initiation of quick ROI calculations.

The above described procedure enables a user to readily identify tissue/blood interfaces on succeeding display frames. However, for the user to then calculate bloods volume, the area enclosed within the actual tissue/blood boundary must be calculated. This has previously been accomplished, as indicated above, by requiring the user to trace the outline of the tissue/blood boundary as an input to the system, which then performs the necessary calculations. The procedure to be discussed below largely eliminates the requirement for such user tracing action.

Figure 3:
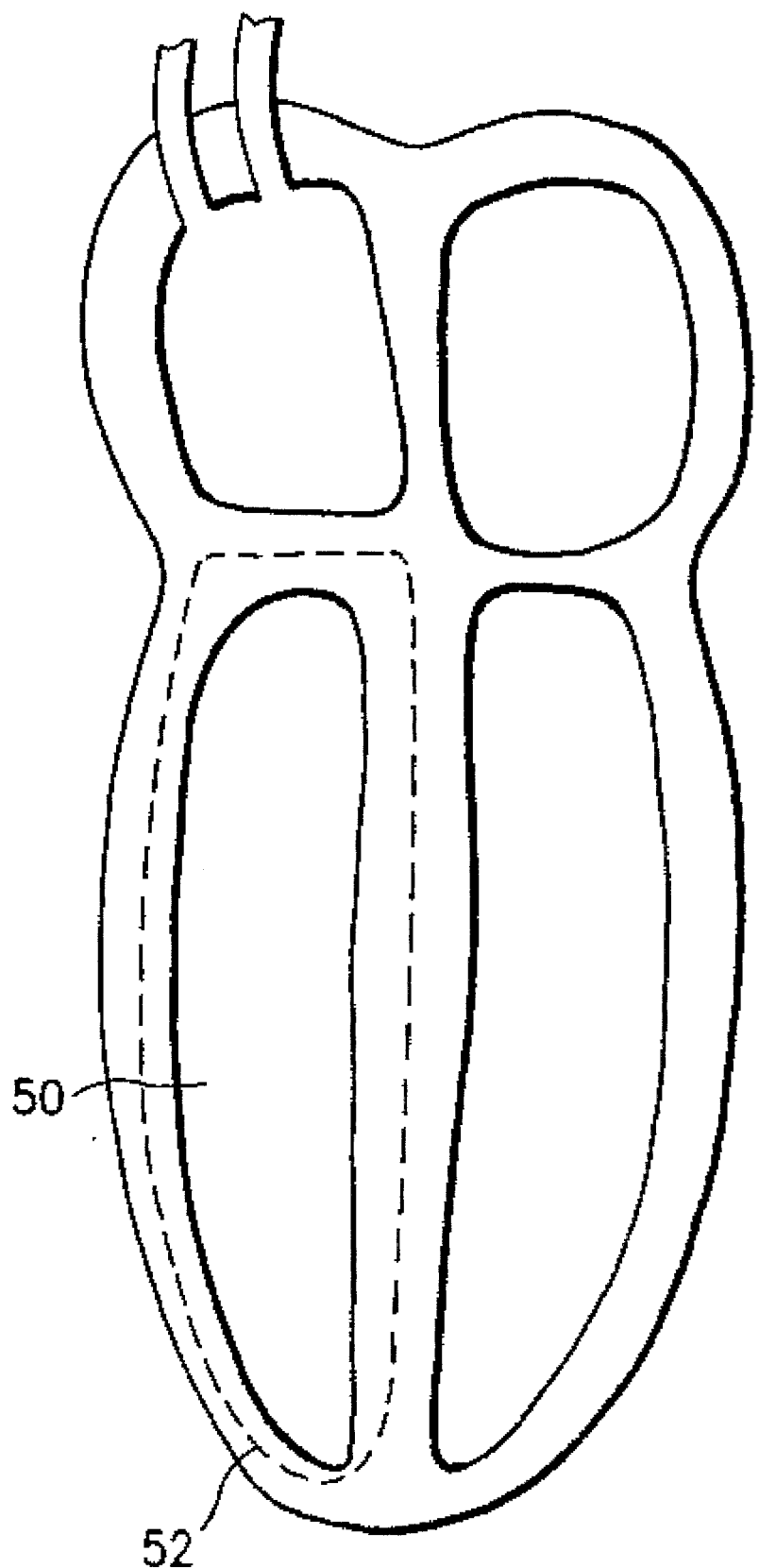
FIG. 3 is a cross sectional view of a heart showing the left ventricle in its fully expanded state.

In FIG. 3, a simplified sectional view of a heart is shown with the left ventricle 50 indicated by quick trace 52. Left ventricle 50 is shown at the end of the diastolic period when the left ventricular volume is at its maximum expansion. In FIG. 3, quick trace 52 defines a half ellipse which is positioned to encompass left ventricle 50. If it is desired to perform a calculation with respect to a lateral cross section of the left ventricle 50, a circular quick trace is preferred.

Figure 4:
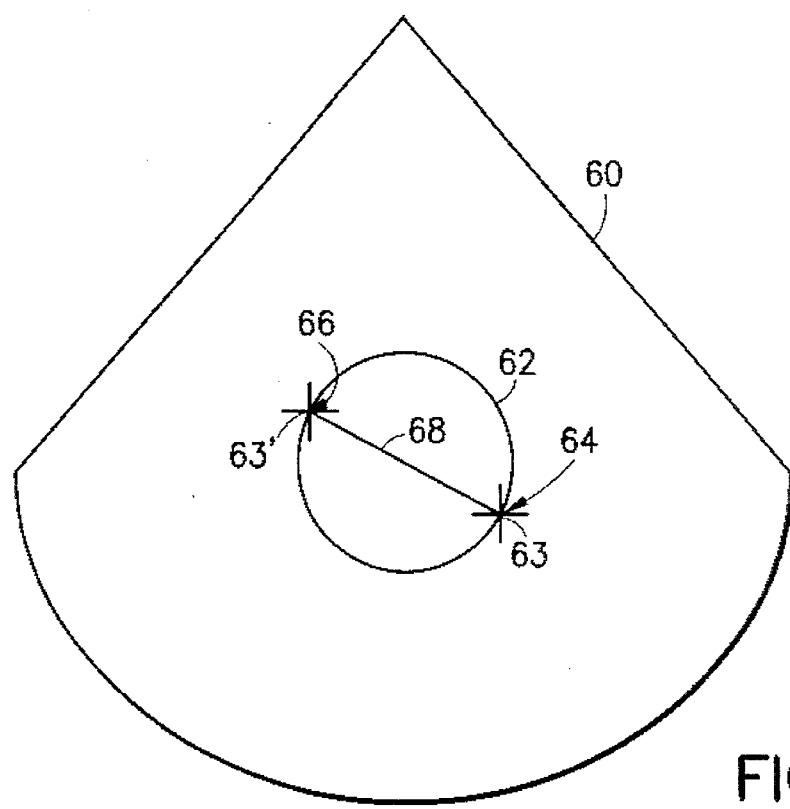
FIG. 4 illustrates a first closed geometric figure that is imposed on the ultrasound display in response to user actuation of a quick ROI procedure.

In FIG. 4, an ultrasound display 60 is caused to have circular quick trace 62 superimposed thereon when a user implements the quick ROI procedure by actuation of quick ROI key 17 (FIG. 1). In brief, the quick ROI procedure initially displays a cursor 63 at a point 64. The user then positions a cursor 63' at an opposing boundary point 66 of an ROI of the displayed ultrasound image (not shown). Entry of cursor 63' at position 66 causes system controller 23 to display a quick trace circle 62 having a diameter 68. The user may then move the position of the cursor 63' (previously at point 66) to another position, and the position of diameter 68 is altered—as is the configuration of circle 62, to accommodate the changed diameter position. The size or position of circle 62 may also be varied by user actuation of Size key 20 or Position key 21 and subsequent actuation of track ball 18 (to be described below).

Figure 5:
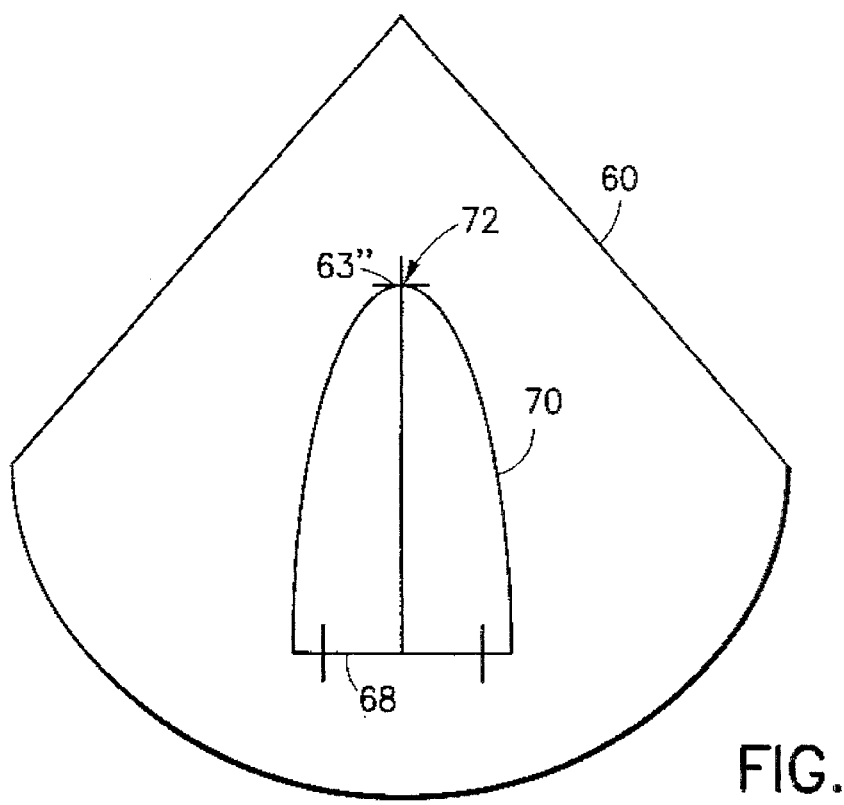
FIG. 5 illustrates a further closed geometric figure which is imposed on the ultrasound display in response to a further actuation of a quick ROI procedure.

In such a manner, a user is enabled to cause quick trace circle 62 to enclose an ROI which is displayed on ultrasound display 60. Further, as shown in FIG. 5, the user is able to impose a quick trace semi-ellipse 70 on ultrasound display 60 and to move the end point 72 of ellipse 70 by moving cursor 63" that is positioned thereat.

Figure 8:
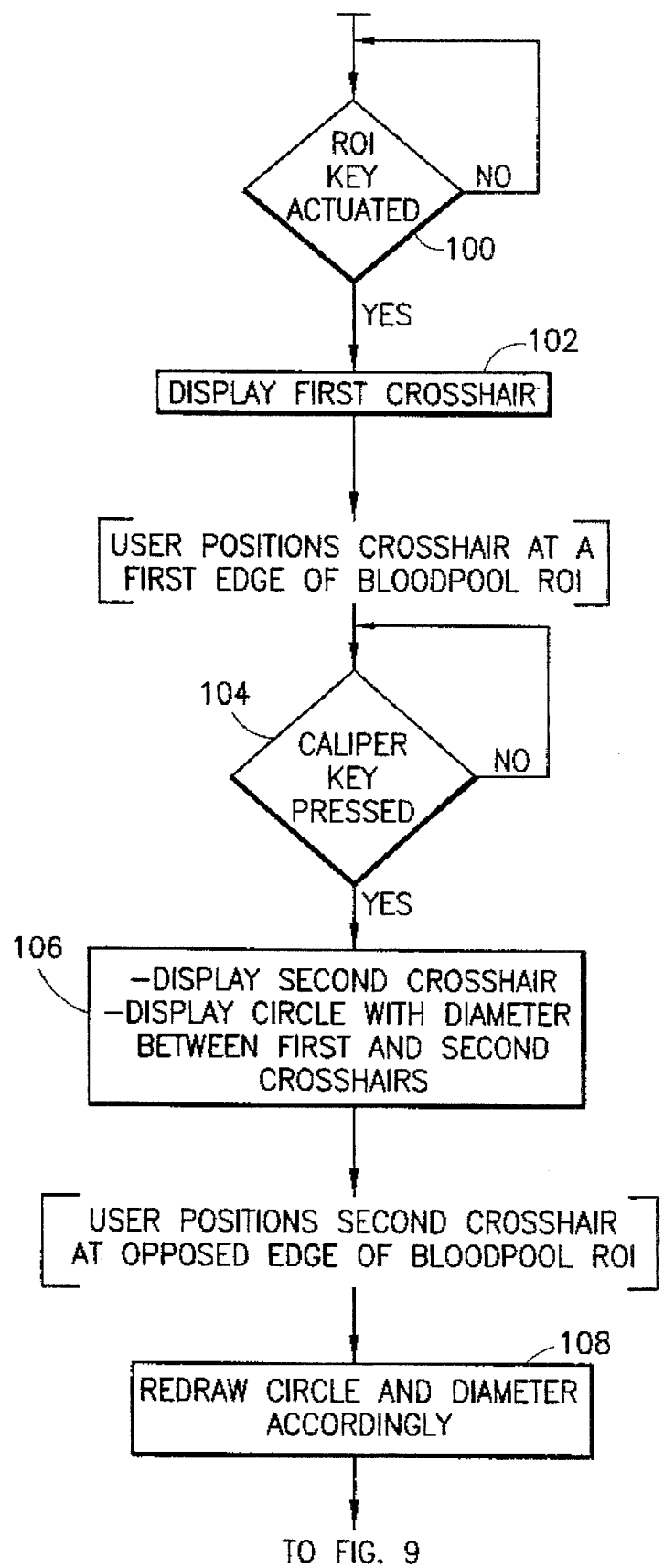
FIGS. 8–10 are flow diagrams illustrating the quick ROI procedure performed by the invention.
Figure 9:
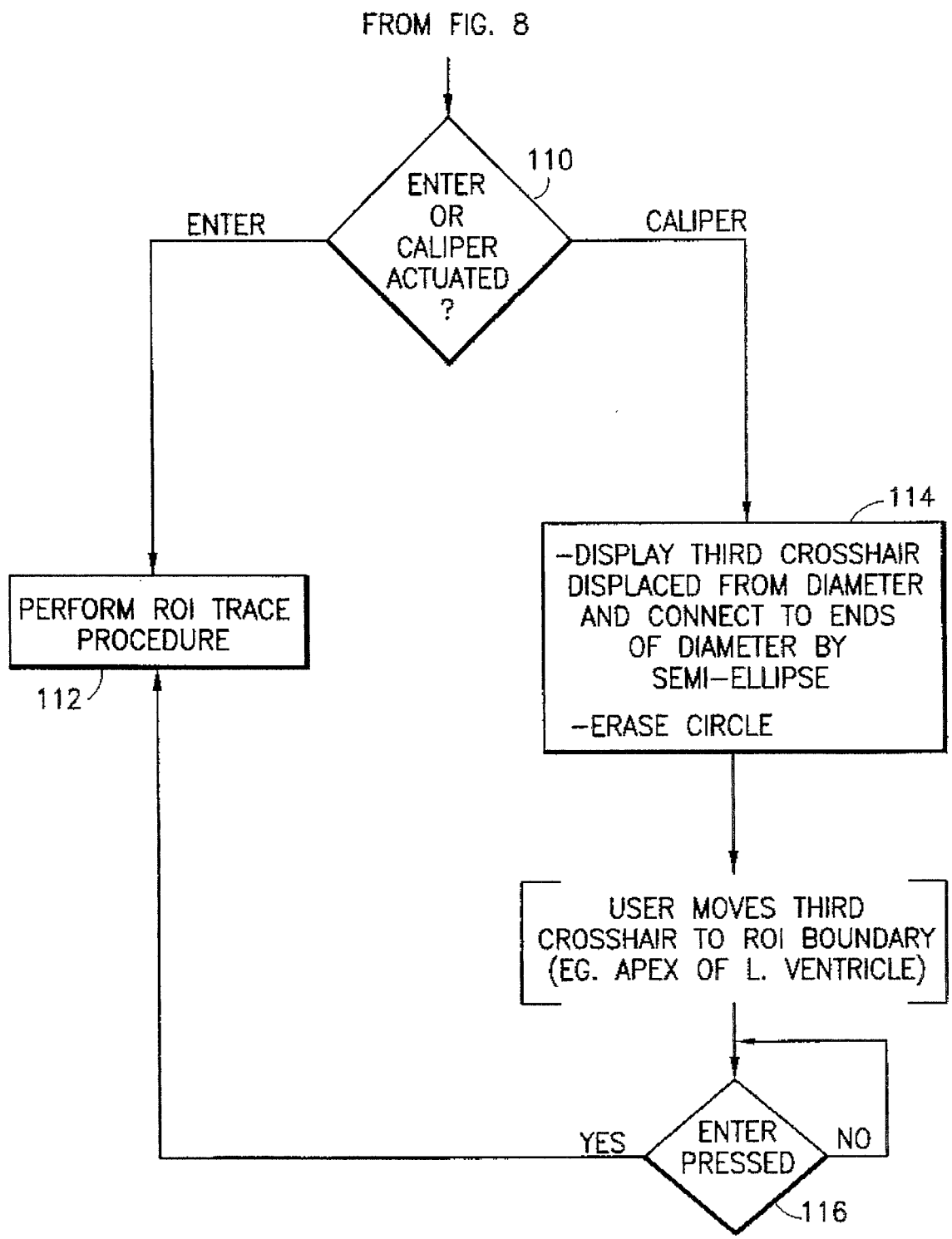
Figure 10:
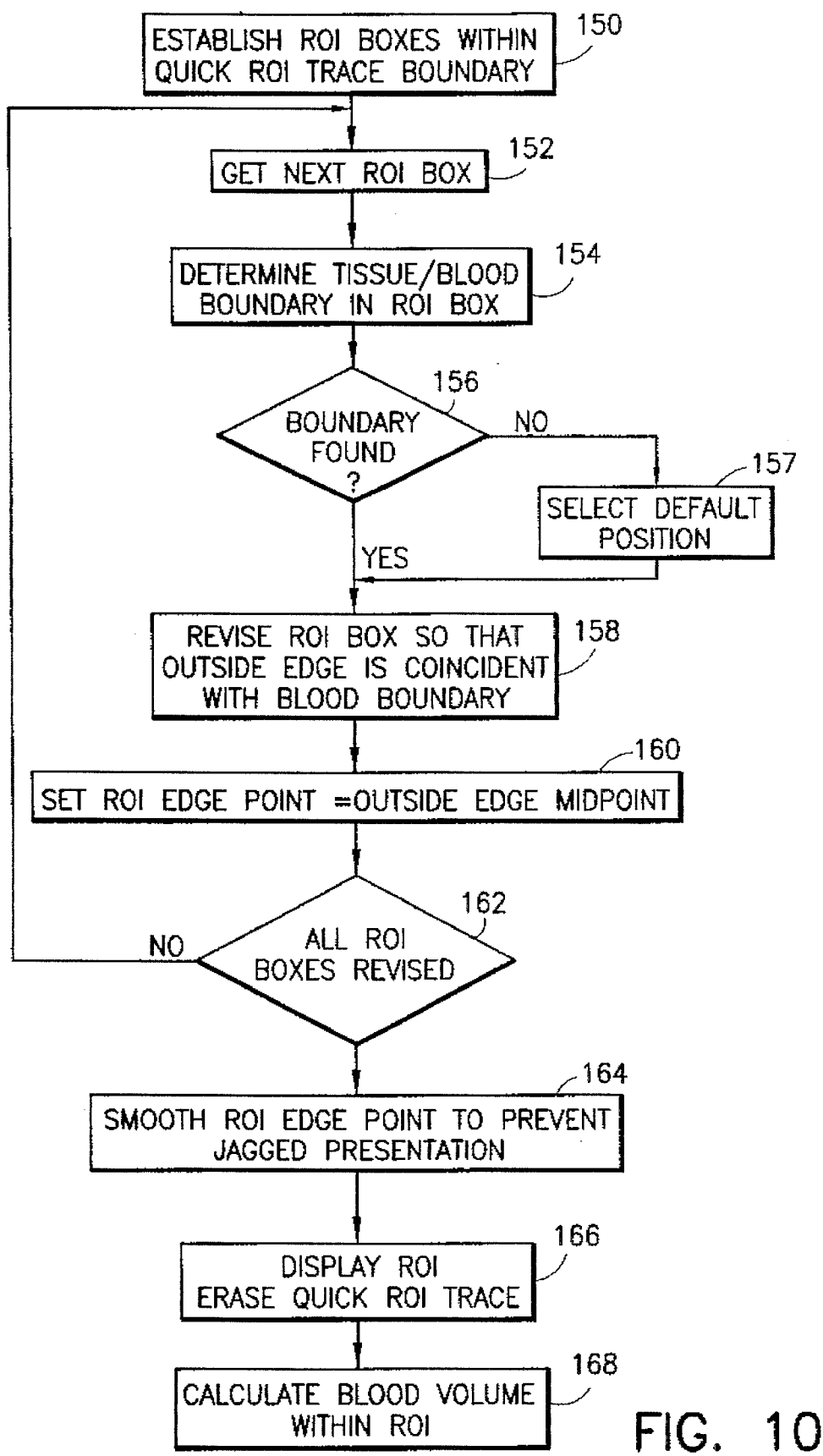

Turning to FIGS. 8–10, the procedure employed by the invention to enable the generation of ROI quick traces will be described in relation to the flow diagrams shown therein. Referring first to FIG. 8, system controller 23 initially awaits the actuation of quick ROI key 17 (decision box 100). Until such actuation occurs, the quick ROI procedure is not initiated. Upon actuation of "ROI" key 17, a crosshair 63 appears on ultrasound display 60 (box 102). Crosshair 63 is initially positioned at point 64. The user is enabled to move the position of crosshair 63 to an edge of a blood pool. Upon being satisfied with the positioning of cursor 63, the user presses a "Caliper" key 19 on keyboard 16 (decision box 104). Until Caliper key 19 is pressed, nothing further occurs. Upon actuation of Caliper key 19, the procedure displays a circle 62 with diameter 68 anchored at one end to crosshair 63 at point 64. At the same time, a second crosshair 63' is displayed at an end point 66 of diameter 68 (box 106). The user is then enabled to reposition crosshair 63' to a further edge point of the blood pool ROI. As the user moves cursor 63', the size and positioning of circle 62 is accordingly altered (box 108).

In a first embodiment of the invention, the user positions circle 62 so that, to the extent possible, the blood pool ROI is within its circumference. As will be hereafter understood, that positioning enables the boundary of the blood pool ROI to be automatically determined.

If the user is satisfied with the positioning of quick trace circle 62, the user actuates an Enter key 22 (decision box 110, FIG. 9) and the procedure moves to perform an ROI trace procedure (to be described below). If, by contrast, the user is interested in performing a calculation with respect to an apical chamber view of a ventricular cavity, in lieu of actuating Enter key 22, the user again actuates Caliper key 19 (decision box 110) which causes erasure of quick trace circle 62 and the display of a quick trace semi-ellipse 70 (FIG. 5), a portion of which passes through a movable crosshair 72. In the case shown in FIG. 5, it is assumed that diameter 68 was previously positioned to coincide with the mitral plane of the left ventricle, enabling quick trace semi-ellipse 70 to extend down the length of the left ventricle towards its apex (box 114). The user may then move the position of crosshair 72 to enable quick trace semi-ellipse 70 to fully encompass the left ventricle. At such point, the user actuates Enter key 22 (box 116) and the procedure moves to the ROI trace procedure (box 112), the details of which are shown in FIG. 10.

Figure 6:
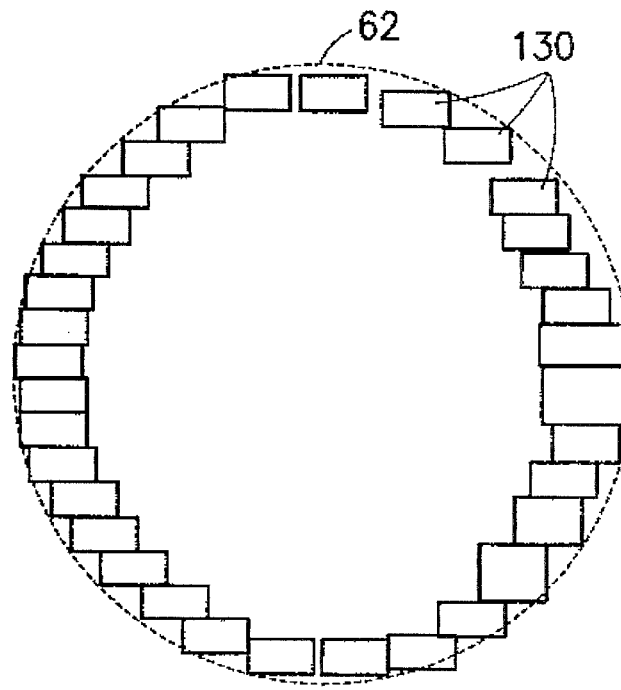
FIG. 6 is a schematic which illustrates a closed geometric figure having plural ROI boxes disposed therein, the ROI boxes enabling a processor to identify an actual ROI boundary.

The ROI trace procedure automatically searches for blood/tissue boundary pixels that lie within the quick ROI trace. When the user positions a quick ROI trace around a blood pool ROI, the user is actually positioning a structure consisting of a number of "ROI boxes" whose outermost edges are coincident with the quick ROI trace. Such a construct is shown in FIG. 6 and comprises quick ROI trace 62 (shown dotted) and a plurality of ROI boxes 130 positioned therein. An ROI box 130 is comprised of four points and is trapezoidal in shape. The four points of each ROI are labeled top—outside, top—inside, bottom—outside and bottom—inside. While the outside and inside edges are parallel, the top and bottom edges do not need to be parallel. The labels are arbitrary and are used to distinguish one point from another in subsequent operations and to keep track of which direction is towards the inside or outside of quick ROI trace 62.

As shown in FIG. 10, the procedure initially establishes the ROI boxes within the quick ROI trace boundary (box 150). Next, a first ROI box is accessed (box 152) and the procedure determines if a tissue/blood boundary falls within the accessed ROI box. This is determined by finding if the ROI box includes a fractional area which contains blood pixels. It will be remembered that each display pixel is assigned a tissue or blood identity. Thus, the procedure examines the assigned identity of each pixel in the ROI box to enable a fractional blood area for the ROI box to be determined. Upon establishing the fractional blood area, a new ROI box is calculated whose total area is equal to the fractional blood area and whose inside edge is the same as the original ROI box. An "actual" blood pool ROI pixel is then calculated to be the pixel at the mid-point of the outside edge of the new ROI box (boxes 158, 160).

Figure 7:
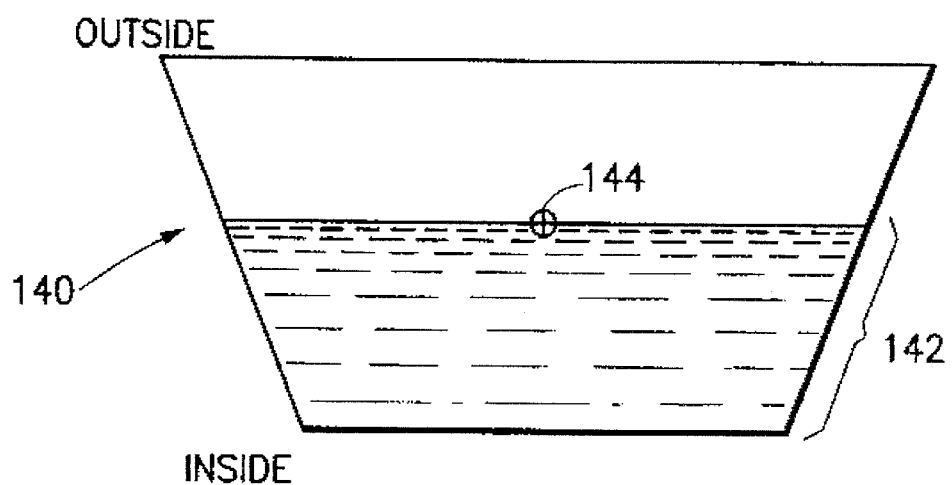
FIG. 7 is a single ROI box which illustrates a trimming action that occurs in response to a determination that an actual ROI boundary point lies within the ROI box.

This procedure can be further appreciated with reference to FIG. 7. There, trapezoid 140 was the original ROI box, and it was determined that portion 142 thereof was comprised entirely of blood pixels. In such case, an actual blood pool ROI pixel 144 is assigned which is the mid-point of the outside edge of blood region 142.

Returning to FIG. 10, it has been assumed that a blood/tissue boundary was in fact found in an ROI box 130. If no such boundary is found (decision box 156), then a default position is assumed for the blood/tissue boundary and an actual ROI point is accordingly assigned (box 157).

If all ROI boxes have not been revised as above noted (decision box 162), the procedure repeats with a next ROI box (box 152). To prevent a jagged presentation, a smoothing algorithm may be employed (box 164). Thereafter, the actual blood pool ROI boundary is displayed using a different color and the quick ROI trace is erased (box 166). Since all ROI boxes have been revised, the actual blood pool/ROI volume may be calculated using the blood pixels within the actual blood pool ROI (box 168).

While positioning and size alteration of the quick ROI trace have been described as being controlled by changes of position of displayed crosshairs, Size and Position procedures can be employed which, upon actuation, enable size and position changes of the quick ROI trace by operation of track ball 18. To implement a size change procedure, Size key 20 is actuated. This enables a changing of the size of the quick ROI trace without alteration of the underlying ultrasound image. Actuation of Size key 20 causes a "shadow" quick ROI trace to be displayed. The original quick ROI trace is erased and the user can now alter the size of the shadow quick ROI trace in both x and y directions. Movement of track ball 18 alters the size of the shadow quick ROI trace. Trackball movement away from the user shrinks the y axis; towards the user enlarges the y axis. Trackball movement to the right of the user enlarges the x axis; to the left shrinks the x axis. When the shadow quick ROI trace is the desired size, the user presses either Enter key 22 or Size key 20 to exit the mode. A new quick ROI trace is then displayed coincident with the shadow quick ROI trace and the old quick ROI trace is lost.

To change the quick ROI trace position, Position key 21 is provided. Actuation of Position key 21 enables movement of the quick ROI trace instead of the underlying ultrasound image. Here again, a "shadow" quick ROI trace appears. Trackball movement towards the user moves the shadow quick ROI trace towards the bottom of the screen; away from the user moves the shadow quick ROI trace towards the top of the screen; towards the left moves the shadow quick ROI trace to the left; and to the right moves the shadow quick ROI trace to the right. When the shadow quick ROI trace is in a desired position, the user presses either the Enter key 22 or Position key 21 to exit the positioning mode. A new quick ROI trace is then generated and old quick ROI trace is lost.

It should be understood that the foregoing description is only illustrative of the invention. Various alternatives and modifications can be devised by those skilled in the art without departing from the invention. While circle and semi-ellipse quick traces have been shown as being employed to implement the quick ROI procedure, any other closed geometric figure may also be employed. Further, while it is preferred that the quick ROI trace be positioned just outside of a blood pool ROI, it can also be positioned just inside of a blood pool ROI. In such case, the processing of the ROI boxes would be adjusted accordingly. Lastly, while the invention is optimized for left ventricle applications, it is applicable to ROI determinations for other imaged blood pools. Thus, the present invention is intended to embrace all such alternatives, modifications and variances which fall within the scope of the appended claims.

What is claimed is:

1. An ultrasound display system for enabling a user to rapidly identify a region of interest (ROI) in a displayed ultrasound image without having to hand-trace an outline of said ROI, said ROI manifesting a fluid/tissue boundary defining a fluid volume, said system comprising:

a display;

ultrasound means including processor means for causing said display to manifest an ultrasound image of said fluid volume and said fluid/tissue boundary;

user entry means for controlling a quick ROI procedure, user actuation of said user entry means causing said processor means to display a closed trace about said fluid volume and said fluid/tissue boundary on said displayed ultrasound image, said user entry means further enabling positional adjustment of said closed trace to substantially enclose said fluid volume and said fluid/tissue boundary.

2. The ultrasound display system as recited in claim 1, further comprising:

selection means responsive to user actuation for causing said processor means to identify a boundary of said ROI that lies in juxtaposition to a boundary of said closed trace and to enable calculations with respect to said ROI.

3. The ultrasound display system as recited in claim 2, wherein said processor means identifies said boundary of said ROI that lies within said closed trace and displays an actual ROI trace determined through use of said closed trace.

4. The ultrasound display system as recited in claim 2, wherein said processor means displays a circle as said closed trace, said user entry means, under control of a user, enabling alteration of a size or position of said circle with respect to said displayed ultrasound image.

5. The ultrasound display system as recited in claim 2, wherein said processor means displays a semi-ellipse, said user entry means, under user control, enabling alteration of a size or position of said semi-ellipse with respect to said displayed ultrasound image.

6. The ultrasound display system as recited in claim 2 wherein said processor means causes said identified boundary of said ROI to be emphasized on said display so as to be distinctly user-visible.

7. A method for causing an ultrasound display system, including a processor, to display an ultrasound image including a region of interest (ROI) manifesting a fluid/tissue boundary defining a fluid volume and to rapidly identify said ROI without requiring a user to hand-trace the fluid/tissue boundary, said method comprising the steps of:

a. positioning a first indicator on a display of said ultrasound image;

b. positioning at least a second indicator on said display;

c. displaying a closed trace that includes said first indicator and said second indicator, said enclosed trace encompassing said fluid/tissue boundary and fluid volume;

d. operating said processor to identify said fluid/tissue boundary lying within said closed trace;

e. performing a calculation with respect to said ROI, employing said fluid/tissue boundary of said ROI; and f. enabling a user to adjust a size of said closed trace to encompass said fluid/tissue boundary.

8. The method as recited in claim 7 wherein step (b) further includes the substep of:

b1. displaying a line between said first indicator and said second indicator and displaying a third indicator offset from said line;

and step (f) includes the substep of:

f1. enabling a user to adjust a size of said closed trace by movement of said third indicator, said closed trace being adjusted to encompass said first indicator, second indicator and third indicator.

9. The method as recited in claim 7, wherein said ultrasound image includes a blood pool within tissue walls, including the further step of:

classifying pixels of said ultrasound image as either blood or tissue;

and step (d) comprises the substeps of d1 creating a plurality of box-like areas about a periphery of said closed trace;

d2 identifying at least a portion each box-like area that comprises blood pixels;

d3 redefining each box-like area to encompass said portion comprising blood pixels; and d4 displaying said boundary of said ROI by employing a pixel on an edge of each redefined box-like area.

10. The method as recited in claim 9 wherein step d1 creates said box-like areas within and bordering on said closed trace.

* * * * *